(12) United States Patent
Gentile et al.

(10) Patent No.: US 6,296,929 B1
(45) Date of Patent: ***Oct. 2, 2001

(54) ABSORBENT MEMBER EXHIBITING EXCEPTIONAL EXPANSION PROPERTIES WHEN WETTED

(75) Inventors: Victor Michael Gentile, Appleton; James Jay Tanner, Winneconne, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/290,323

(22) Filed: Apr. 12, 1999

(51) Int. Cl.$^7$ ........................................ B32B 7/02
(52) U.S. Cl. .................. 428/218; 604/367; 604/374; 604/375
(58) Field of Search ........................ 604/385.01; 162/100, 162/109; 428/171

(56) References Cited

U.S. PATENT DOCUMENTS

| | | | |
|---|---|---|---|
| 3,512,530 | 5/1970 | Jones, Sr. | 128/290 |
| 3,736,931 | 6/1973 | Glassman | 128/290 R |

(List continued on next page.)

FOREIGN PATENT DOCUMENTS

| | | |
|---|---|---|
| 0 293 208 B1 | 7/1991 | (EP) . |
| 0 804 912 A1 | 11/1997 | (EP) . |
| 0 804 913 A1 | 11/1997 | (EP) . |
| 0 804 916 A1 | 11/1997 | (EP) . |
| 0 804 917 A1 | 11/1997 | (EP) . |
| WO 96/38232 A1 | 12/1996 | (WO) . |

OTHER PUBLICATIONS

Derwent World Patent Database abstract of JP 92–08787 A: Description of Daiwa Kagaku Kogyo KK; Sanyo Chem Ind. Ltd., "Antimicrobial Water–Absorbing Resin Composition For Packaging."

"Absorbent Core Technology for Personal Care Products," *Teltech Research Services Monthly Update*, Mar. 1999, pp. 1–8.

*Primary Examiner*—Terrel Morris
*Assistant Examiner*—Christopher C. Pratt
(74) *Attorney, Agent, or Firm*—Thomas J. Connelly

(57) ABSTRACT

An absorbent member is disclosed which has a high absorbent capacity and which exhibits exceptional expansion properties when wetted by an aqueous fluid. The absorbent member includes a multitude of randomly oriented cellulosic fibers having an average length of from between about 1 mm to about 5 mm and containing at least about 20% lignin within each fiber. The absorbent member also has a moisture content of from between about 1% to about 20% water by weight of fiber and has a density in the range of from between about 0.1 g/cc to about 1 g/cc. The fibers are stressed and bonded by hydrogen bonds and are retained in an elastically stressed condition.

18 Claims, 9 Drawing Sheets

U.S. PATENT DOCUMENTS

| | | | |
|---|---|---|---|
| 3,844,288 | 10/1974 | Kiela | 128/287 |
| 4,057,061 | 11/1977 | Ishikawa et al. | 128/284 |
| 4,100,324 | 7/1978 | Anderson et al. | 428/288 |
| 4,215,212 * | 7/1980 | Franks | 536/57 |
| 4,275,811 | 6/1981 | Miller | 206/204 |
| 4,321,997 | 3/1982 | Miller | 206/204 |
| 4,382,507 | 5/1983 | Miller | 206/204 |
| 4,410,578 | 10/1983 | Miller | 428/117 |
| 4,537,655 | 8/1985 | Henriksson et al. | 162/23 |
| 4,544,596 * | 10/1985 | Holtman | 428/171 |
| 4,560,527 | 12/1985 | Harke et al. | 264/500 |
| 4,619,862 | 10/1986 | Sokolowski et al. | 428/221 |
| 4,621,011 | 11/1986 | Fleischer et al. | 428/221 |
| 4,735,846 | 4/1988 | Larsonneur | 428/198 |
| 4,770,920 | 9/1988 | Larsonneur | 428/198 |
| 4,822,452 | 4/1989 | Tse et al. | 162/146 |
| 4,879,170 | 11/1989 | Radwanski et al. | 428/233 |
| 4,931,355 | 6/1990 | Radwanski et al. | 428/283 |
| 4,940,621 | 7/1990 | Rhodes et al. | 428/137 |
| 4,950,262 | 8/1990 | Takagi | 604/385.1 |
| 5,022,945 | 6/1991 | Rhodes et al. | 156/253 |
| 5,055,332 | 10/1991 | Rhodes et al. | 428/74 |
| 5,137,537 | 8/1992 | Herron et al. | 8/120 |
| 5,183,707 | 2/1993 | Herron et al. | 428/364 |
| 5,242,435 | 9/1993 | Murji et al. | 604/374 |
| 5,295,986 | 3/1994 | Zehner et al. | 604/385.1 |
| 5,320,895 | 6/1994 | Larsonneur et al. | 428/137 |
| 5,374,260 | 12/1994 | Lemay et al. | 604/378 |
| 5,387,385 | 2/1995 | Murji et al. | 264/160 |
| 5,399,412 | 3/1995 | Sudall et al. | 428/153 |
| 5,409,572 * | 4/1995 | Kershaw et al. | 162/109 |
| 5,415,644 | 5/1995 | Enloe | 604/385.2 |
| 5,466,232 | 11/1995 | Cadieux et al. | 604/378 |
| 5,484,896 | 1/1996 | Naieni et al. | 530/504 |
| 5,492,753 | 2/1996 | Levy et al. | 428/219 |
| 5,549,791 | 8/1996 | Herron et al. | 162/157.6 |
| 5,582,606 | 12/1996 | Bruemmer et al. | 604/385.2 |
| 5,620,431 | 4/1997 | LeMahieu et al. | 604/385.2 |
| 5,634,915 | 6/1997 | Osterdahl | 604/379 |
| 5,649,918 | 7/1997 | Schleinz | 604/385.2 |
| 5,672,248 | 9/1997 | Wendt et al. | 162/109 |
| 5,703,225 | 12/1997 | Shet et al. | 536/59 |
| 5,728,085 | 3/1998 | Widlund et al. | 604/378 |
| 5,730,737 | 3/1998 | Widlund et al. | 604/378 |
| 5,779,860 | 7/1998 | Hollenberg et al. | 162/206 |
| 5,814,034 | 9/1998 | Widlund et al. | 604/367 |
| 5,817,085 | 10/1998 | Widlund et al. | 604/379 |
| 5,998,032 * | 12/1999 | Hansen et al. | 428/403 |

* cited by examiner

ABSORBENT MEMBER EXHIBITING EXCEPTIONAL EXPANSION PROPERTIES WHEN WETTED

FIELD OF THE INVENTION

This invention relates to an absorbent member having a high absorbent capacity and exhibiting exceptional expansion properties when wetted. More specifically, this invention relates to an absorbent member exhibiting exceptional expansion properties when wetted by an aqueous solution.

BACKGROUND OF THE INVENTION

Most traditional absorbent structures consist of a static network of fibers which contain a plurality of open areas located between the fibers. The open areas retain aqueous fluid which is absorbed by the absorbent structure. The majority of fluid is not absorbed into each individual fiber but instead most fluid is retained within the empty spaces which are formed in the network of cellulosic fibers. If the traditional absorbent member has a high absorbent capacity it usually does not have a high wicking rate. The reason for this is that the first attribute is in conflict with the second attribute.

Efforts to find absorbent members which have both a high absorbent capacity as well as a high wicking rate have only been marginally successful. It has been recognized that the dynamic properties of the fibers themselves somehow have to be changed. Some success has been obtained in calendering a wet laid network of bleached chemi-thermo-mechanical pulp (BCTMP). For this material, small expansion or release of potential energy upon wetting of the absorbent fibers was observed which can enhance the absorbent capacity and wicking rate of the absorbent member. It is believed that this occurs because the absorbent fibers are oriented, to a large extent, in the horizontal plane but with some modest "z" direction to the fiber axis as they conform to an irregular surface of the forming wire. The high to low position of the forming wires is about 0.020 to about 0.025 inches (about 0.508 mm to about 0.635 mm). When the tissue sheet is hot calendered at high pressure, this high to low shaping (or bumps in the sheet) is smoothed out. It is believed that the heat mobilizes any water present in the fibers, and the close proximity of fiber surfaces (intra and inter) allows hydrogen bonds to form with very little water present. When the flattened sheet is exposed to water, the hydrogen bonds break and the fibers return to their original shape. Since the wet laid sheet has a wet strength agent added, e.g., Kymene, the fibers stay attached to each other in the network therefore the sheet returns to its original bumpy state before calendering. These bumps or pockets on the surfaces hold more moisture than the flat sheet but a large portion of that moisture is not bound within the sheet structure.

It has also been observed that the open spaces within the fiber structure (void volume) of most traditional absorbent members, such as a paper towel, is limited. This is primarily due to two characteristics. First, the traditional absorbent member is restricted from expanding by the presence of wet strength bonds which limit or reduce the ability of the absorbent member to expand. Second, the axis of fibers of a traditional absorbent member are essentially oriented in only the x and y directions, not in the z-direction. This limits the absorbent member from being able to expand in three directions, thus reducing both its absorbent capacity and wicking rate.

Other attempts to increase the absorbent capacity and wicking rates of a traditional absorbent member have included the addition of superabsorbent particles (SAP). Superabsorbent particles have the ability to expand in size as they absorb fluid and also have the ability to retain fluid. However, the use of superabsorbent particles is disadvantageous in that most are very expensive and some of them tend to be rather slow in absorbing fluid. In addition, the relative absorbent capacity of most superabsorbent material is adversely affected by pressure and by ionic salts which are present in certain aqueous fluids, such as urine. Therefore, they present certain drawbacks to being used in disposable absorbent products such as diaper, training pants, incontinence garments, feminine napkins, meat and poultry pads, and the like.

Now it has been recognized that there is a real need for an absorbent member which has both a high absorbent capacity and a high wicking rate as well as the ability to rapidly expand in at least one direction when wetted by an aqueous fluid.

SUMMARY OF THE INVENTION

Briefly, this invention relates to an absorbent member which has a high absorbent capacity and which exhibits exceptional expansion properties when wetted by an aqueous solution. The absorbent member is constructed from a multitude of randomly oriented cellulosic fibers containing at least about 20% lignin within the fibers. The fibers have an average length of from between about 1 mm to about 5 mm. The absorbent member can have a moisture content of between about 1% to about 20% water by weight of fiber and has a density in the range of between about 0.2 g/cc to about 1 g/cc. The fibers are stressed or strained and bonded together by hydrogen bonds (both intra and inter fiber bonds) which constrain the fibers in an elastically stressed condition.

The general object of this invention is to provide an absorbent member having a high absorbent capacity and which exhibits exceptional expansion properties when wetted. A more specific object of this invention is to provide an absorbent member which exhibits exceptional expansion properties when wetted by an aqueous solution.

Another object of this invention is to provide an absorbent member which is capable of rapidly expanding in a selected direction opposite to the direction of a force vector used to induce the stressed or strained condition.

A further object of this invention is to provide an absorbent member which can expand against significant resisting force or pressure.

Still another object of this invention is to provide an absorbent member which is easy to construct and relatively inexpensive.

Still further, an object of this invention is to provide an absorbent member which exhibits a rapidly changing capillary structure when wetted by an aqueous solution.

Other objects and advantages of the present invention will become more apparent to those skilled in the art in view of the following description and the accompanying drawings.

DETAILED DESCRIPTION OF THE PREFERRED EMBODIMENT

Figure 1:
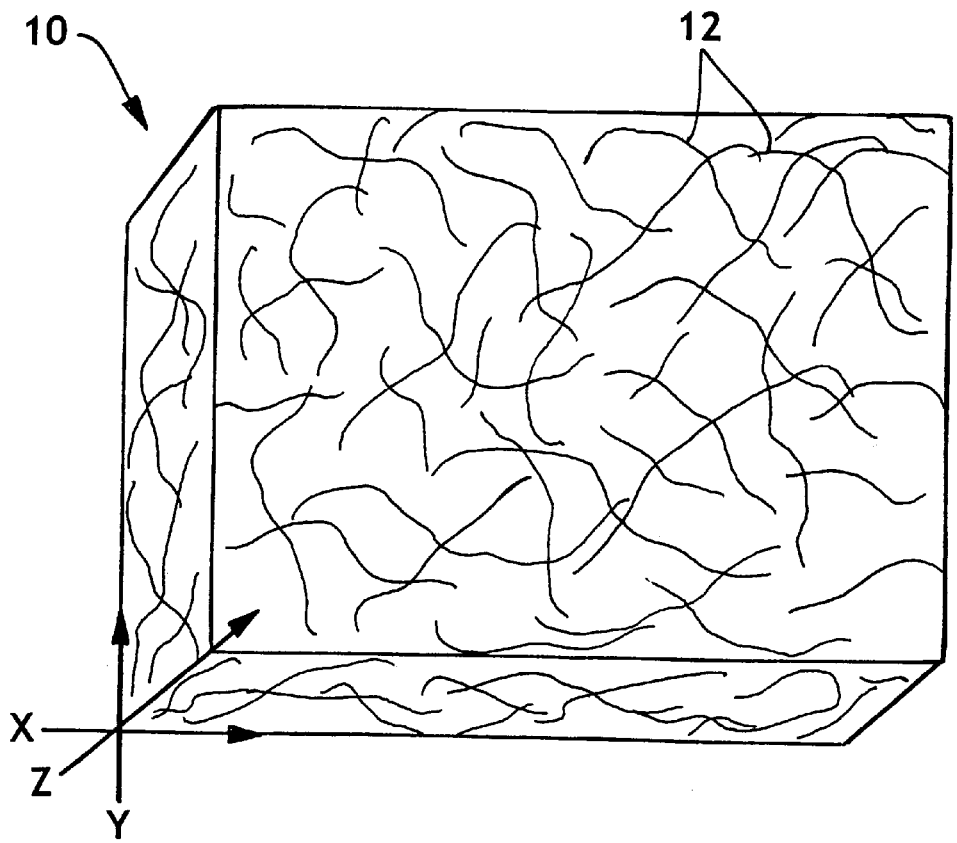
FIG. 1 is a perspective view of an absorbent member of this invention exhibiting a multitude of randomly oriented cellulosic fibers present in the x, y and z directions.

Referring to FIG. 1, an absorbent member 10 is shown which is constructed from a multitude of randomly oriented cellulosic fibers 12. The absorbent member 10 has a high absorbent capacity and exhibits exceptional expansion properties when wetted by an aqueous fluid, such as water. The fibers 12 have an average length of from between about 1 mm to about 5 mm and are preferably cellulosic softwood fibers which are relatively stiff. The fibers 12 are randomly oriented and elastically stressed or strained in one or more selected directions. Preferably, the fibers 12 are chemi-thermo-mechanical softwood fibers, and most preferably, they are bleached chemi-thermo-mechanical softwood fiber. The bleaching masks the yellow color which occurs because of the high percentage of lignin which is retained within each fiber.

Preferably, the fibers 12 should be non-linear in configuration. At least a majority of the fibers 12 should be non-linear in configuration and exhibit a curved, bent, crimped, kinked, arcuate, contorted, curled or some other non-linear shape. By "kinked" it is meant a tight bend or a sharp twist in a tube-like fiber. It should be noted that the entire fiber does not have to be curved, bent, crimped, kinked, etc. but that at least a portion of the fiber should exhibit a non-linear geometrical shape. The more each fiber 12 is contorted or formed into a non-linear shape, the better the absorbent properties of the absorbent structure 10. Linear fibers can be used but they should only represent a minority of the overall fibers present. Preferably, less than 40% of the fibers 12 should be linear.

Each fiber 12 should contains at least about 20% lignin and with the remaining 80% being cellulosic materials which includes cellulose plus hemicellulose and other minor wood components. Lignin is the chief non-carbohydrate constituent of wood and other fibrous plants. Lignin is a polymer which functions as a natural binder and provides support for the cellulosic fibers. The lignin is present both within each fiber and between adjacent fibers. For purposes of this invention, it is important that the required percent of lignin be present within each fiber 12. The presence of the lignin within each fiber 12 makes the fibers 12 stiffer and more difficult to bend. This is a major difference from traditional unbonded cellulosic absorbent fibers which are typically bleached southern softwood Kraft fibers which contain very little if any lignin within the fiber itself. Hence, the traditional fibers are soft and limp. Lignin functions as a thermoplastic reinforcing material which allows the fibers to return to a natural tubular state upon wetting. Cellulose and hemicellulose give the fibers hydrophilic properties and the ability to form hydrogen bonds in the presence of small amounts of water.

One will notice from viewing FIG. 1 that the fibers 12 are randomly oriented and densely compacted. The primary axis of each fiber can be oriented in the x-direction, in the y-direction or in the z-direction. This three dimensional, random orientation is beneficial in creating a high absorbent capacity and a high wicking rate within the absorbent member 10. To the contrary, most traditional fibers which have been wet-laid into a fibrous sheet have virtually all of the fibers laid with their long axis in the x-y plane and a significant number of the fibers lie in the machine direction (MD) or x-direction. Essentially none of the wet-laid fibers are oriented in the vertical or z-direction.

The fibers 12 of this invention are stressed into an extremely compacted condition to form an entangled mass which is held together by a plurality of hydrogen bonds. Some of the fibers 12 are held in compression, some in bending and some in shear. These can be both inter fiber hydrogen bonds and intra fiber hydrogen bonds. This is an environment wherein almost every fiber 12 is retained in a stressed or non-relaxed condition. The stress forces may be applied in more than one direction.

Figure 2:
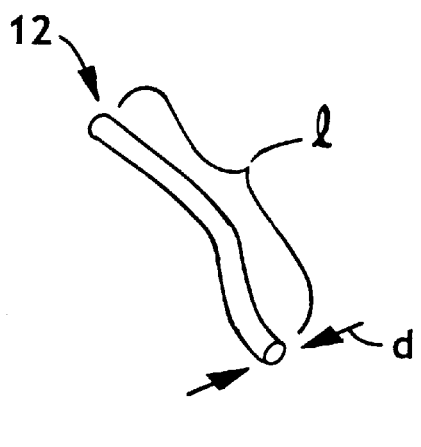
FIG. 2 is a perspective view of an individual cellulosic fiber.

Referring now to FIG. 2, an individual fiber 12 is depicted having a diameter "d" of less than about 50 microns, preferably a diameter "d" of from between about 10 to about 40 microns, and most preferably, a diameter "d" of from between about 20 to about 30 microns. Each fiber 12 also has a length "l" of less than about 5 millimeters, preferably the length "l" is from between about 1 to about 5 millimeters, and most preferably, the length "l" is from between about 1 to about 3 millimeters. As with most natural materials, there is a distribution of properties, so that stated dimensions do not limit this invention.

Each cellulosic fiber 12 has a moisture content of from between about 1% to about 20% water by weight of fiber.

Preferably, the moisture content of each fiber 12 is from between about 2% to about 15% water by weight of fiber, and most preferably, the moisture content of each fiber 12 is from between about 5% to about 15% water by weight of fiber. This level of moisture is required to obtain hydrogen bonding. However, the absorbent member 10 could be heated until dry after bonding where the moisture level within the absorbent has essentially dropped to zero. The cellulosic fibers 12 in a non-stressed, unbonded condition have a bulk density of at least 0.01 grams per cubic centimeter (g/cc). Preferably, the bulk density of all the non-stressed fibers 12 is from between about 0.02 g/cc to about 0.1 g/cc, and most preferably, the bulk density of all the non-stressed fibers 12 is from between about 0.05 g/cc to about 0.08 g/cc. The low bulk density of the cluster of non-stressed, unbonded fibers allows for a high level a stress to be induced into the fibers just before bonding them together.

Referring again to FIG. 1, it should be noted that the absorbent member 10, when the cellulosic fibers 12 are in a stressed condition, will have a density, sometimes referred to as "bulk density," of from between about 0.2 g/cc to about 1 g/cc. Preferably, the bulk density of the absorbent member 10 is between about 0.2 cc to about 0.8 g/cc, and most preferably, the bulk density of the absorbent member 10 is between about 0.5 g/cc to about 0.8 g/cc. This density is still below the density of the cellulose walls of the individual fibers 12 which is approximately 1.4 g/cc. Therefore, there is still a significant but reduced amount of open space in the stressed and bonded absorbent member 10, about 33% versus 98.6% for an unstressed and unbonded air laid absorbent structure of fibers.

Figure 3:
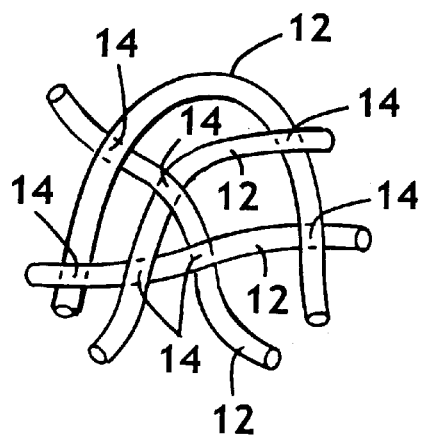
FIG. 3 is a perspective view of four randomly oriented fibers which are bonded together by hydrogen bonds.

Referring now to FIG. 3, four randomly oriented fibers 12 are shown bonded together by a multitude of hydrogen bonds 14. A hydrogen bond is a weak chemical bond formed between an electronegative oxygen atom and a hydrogen atom already bonded to another electronegative oxygen atom. The hydrogen bonds 14 cause the fibers surfaces 12 to be attached to adjacent fiber surfaces. Hydrogen bonding will occur within fibers as well. This condition can occur when, for example, a tubular fiber is twisted or bent and the circular open lumen cross-section collapses to a flattened elliptical shape. When the two or more different points inside the lumen touch or are forced together under pressure or stress hydrogen bonding can occur. In the elastically stressed and bonded condition, the fibers 12 exhibit stored bending, compression and shear energy. Hydrogen bonds 14 form as the fiber surfaces 12 are brought into intimate contact under pressure. Water that is in or on the individual fibers 12 contribute to the intimate contact and formation of the bond even though there is still more liquid capacity in and around the fibers (not saturated). As water leaves the contact point between the fibers 12 due to drying or migration to drier areas, surface tension makes two adjacent fibers or two areas or points inside a fiber lumen come closer together allowing hydrogen bonding to occur. The moisture of the absorbent member 10 should be less than about 15% water per unit weight of fiber, and preferably, from between about 5% to about 10% water per unit weight of fiber to allow enough hydrogen bonds to form to lock in the stressed high density condition. Insufficient moisture would inhibit hydrogen bond formation according to the mechanism described, while excessive moisture would disrupt the hydrogen bonds upon release of the stressing forces.

The hydrogen bonds 14 are relatively weak bonds but they are plentiful and sufficiently strong to lock in the stresses created in and between the fibers 12 as the fibers 12 are stressed into an extremely compacted form of the absorbent member 10. One method of constructing the absorbent member 10 is to collect randomly oriented fibers 12 in a hopper or vessel and then compress the fibers 12 from a single direction into a sheet of fibers. Experimental testing has indicated that when the cellulosic fibers 12 are compressed in only one direction, say vertically in the z-direction, then when the absorbent member 10 is later wetted by an aqueous fluid such as water, the greatest expansion will occur in a single direction opposite to the direction from which the fibers 12 were compressed.

Experimental testing has also revealed that the fibers 12 can be compressed from two or more directions, either simultaneously or sequentially, and the absorbent member 10 formed in this fashion will experience rapid expansion, when wetted by an aqueous fluid, in the two or more directions opposite to the directions of compression. This feature is important for it will allow a manufacturer to construct an absorbent member 10 which can be tailored to the environment in which it is designed to function. For example, if the absorbent member 10 is constructed for use in an infant's diaper, and the physical size and geometry of its placement in the diaper requires expansion in the y and z directions (i.e., radial expansion), then the absorbent member 10 can be compressed during formation only in these two directions. During use in the diaper, the absorbent member 10 will experience very little expansion in the x-direction but will exhibit substantial and rapid expansion in both the y and z-directions (or radial direction). The usefulness of being able to construct an absorbent member 10 with such expansion properties will be readily apparent to those skilled in the art of disposable absorbent products.

It has been mentioned earlier that the expansion occurs as the absorbent member 10 is wetted by an aqueous fluid. Aqueous fluids are defined for purposes of this invention as fluids which contain water or are similar to water. Representative fluids include tap water, distilled water, bottled water, urine, menses, human body fluids, emulsions of water plus hydrocarbons, etc. It should also be noted that non-aqueous fluids such as oils, non-polar hydrocarbons, etc. will not trigger the release of hydrogen bonds formed in and between the fibers.

As the absorbent member 10 is wetted, the hydrogen bonds 14 break and the stresses locked up in the individual fibers 12 and the absorbent member 10 are released. This causes the fibers 12 to move toward their original relaxed condition, tubular shape typically in a direction opposite to the direction from which they were stressed or compressed. As more and more hydrogen bonds are broken, more and more fibers 12 are free to flex back to a less stressed or to a relaxed condition. As this occurs, open or void volume develops between the fibers 12. These voids are capable of receiving and containing the fluid which has insulted the absorbent member 10. This increases the absorbent capacity of the absorbent member 10 and the absorbent member 10 becomes capable of receiving and holding larger and larger quantities of fluid. The increased volume of the capillaries between fibers promotes a higher degree of fluid flow and wicking due to reduce friction or fluid drag. Thus, the absorbent member 10 performs differently from any known cellulosic product commercially sold today. Compressed regenerated cellulose sponges perform somewhat similarly but they are much more expensive to produce and cannot exert the pressure level of this invention.

The absorbent member 10 of this invention is unique in that the wet expansion rate is very rapid. The "wet expansion rate" is defined for purposes of this invention as the time it takes for the absorbent member 10 to expand to its maximum, (change in volume/unit time) once it is surrounded by an aqueous fluid, such as water. The wet expansion rate for some portion of the full expansion time can be determined by measuring the slope of the curve established by plotting the change in volume of the absorbent member 10 for each moment in time over the duration of the expansion. The wet expansion rate is related to the bulk density of the absorbent member 10 and to the depth of penetration that the fluid must travel to reach the midpoint or mid plane of the absorbent member 10. For example, a spherical shape, at a high density, denoted by the Greek letter rho "$\rho$", will have a slow maximum expansion rate for it has a low surface area to volume ratio (r) calculated by the formula r=6/d, where d is the diameter of the sphere. This can be contrasted to a thin sheet, like a piece of paper, where a high surface area to volume ratio is found which can be calculated by the formula r=2/t, where t is equal to the thickness of the sheet. The expansion rate for the thin sheet will be faster than for the sphere assuming both have equal weights and equal densities. For a sphere and sheet of paper of equal weight and density, their size relationship can be expressed by the formula d=6 gsm/$\rho$; where d is the diameter of the sphere, "$\rho$" is the density of both shapes, and "gsm" is the basis weight of the thin sheet, e.g. grams per square meter.

Figure 4:
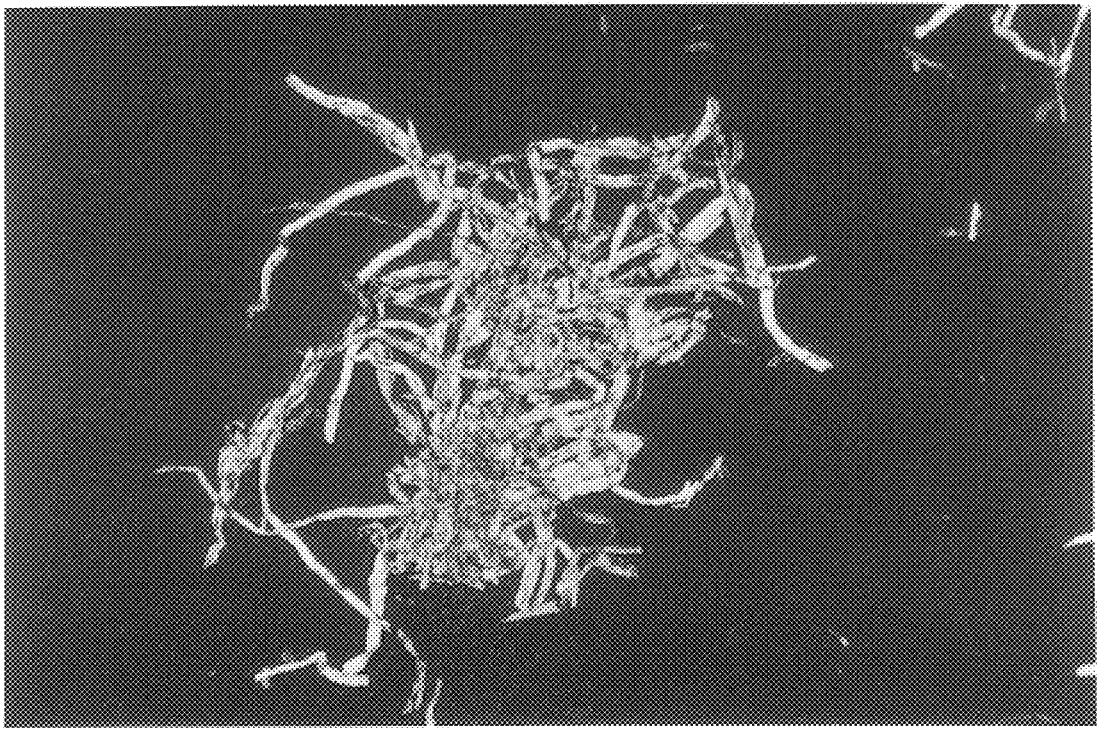
FIG. 4 is a photomicrograph of a bleached chemi-thermo-mechanical pulp fibers in a dry state and taken at 20×magnification.
Figure 5:
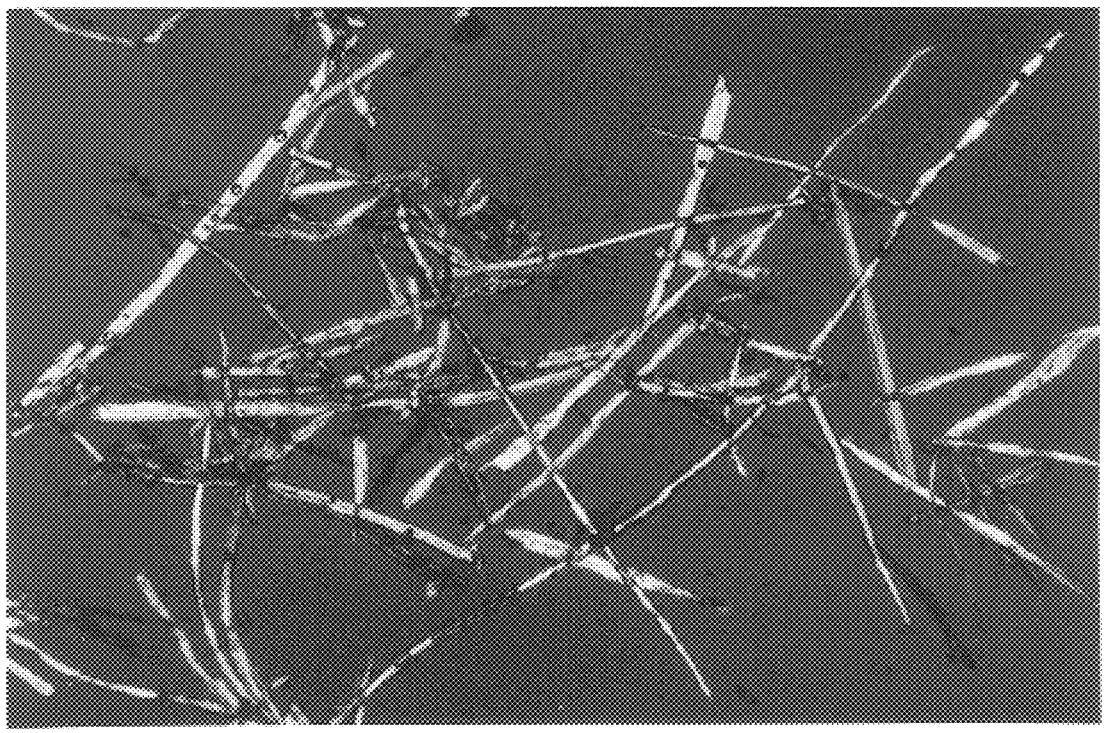
FIG. 5 is a photomicrograph of a bleached chemi-thermo-mechanical pulp fibers after contact with water and taken at 20×magnification.

FIGS. 4 and 5 are optical photomicrographs of BCTMP fibers taken at 20×magnification. FIG. 4 represents the fibers in a dry state while FIG. 5 shows the fibers after they have been contacted with water. One can clearly see that the compressed and stressed fibers in FIG. 4 do return to their pre-compression state in FIG. 5. In FIG. 5, the fibers are more linear in shape, tubular in configuration and individual fibers are generally spaced apart from one another.

Figure 6:
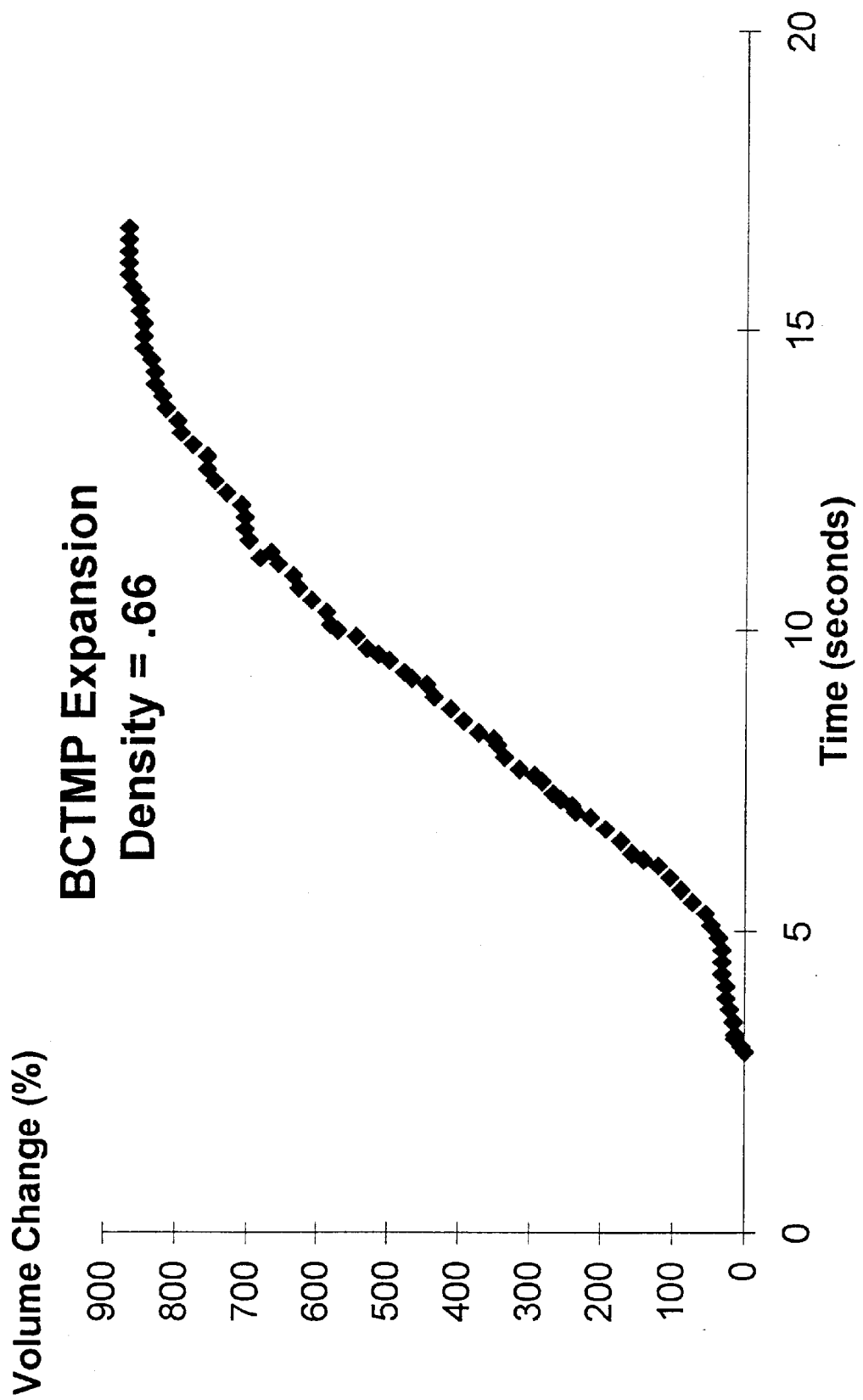
FIG. 6 is a graph of an absorbent member, formed from bleached chemi-thermo-mechanical pulp and having a density of 0.66 g/cc, which compares volume change measured as a percentage along the y-axis, to a change in time measured in seconds along the x-axis.
Figure 7:
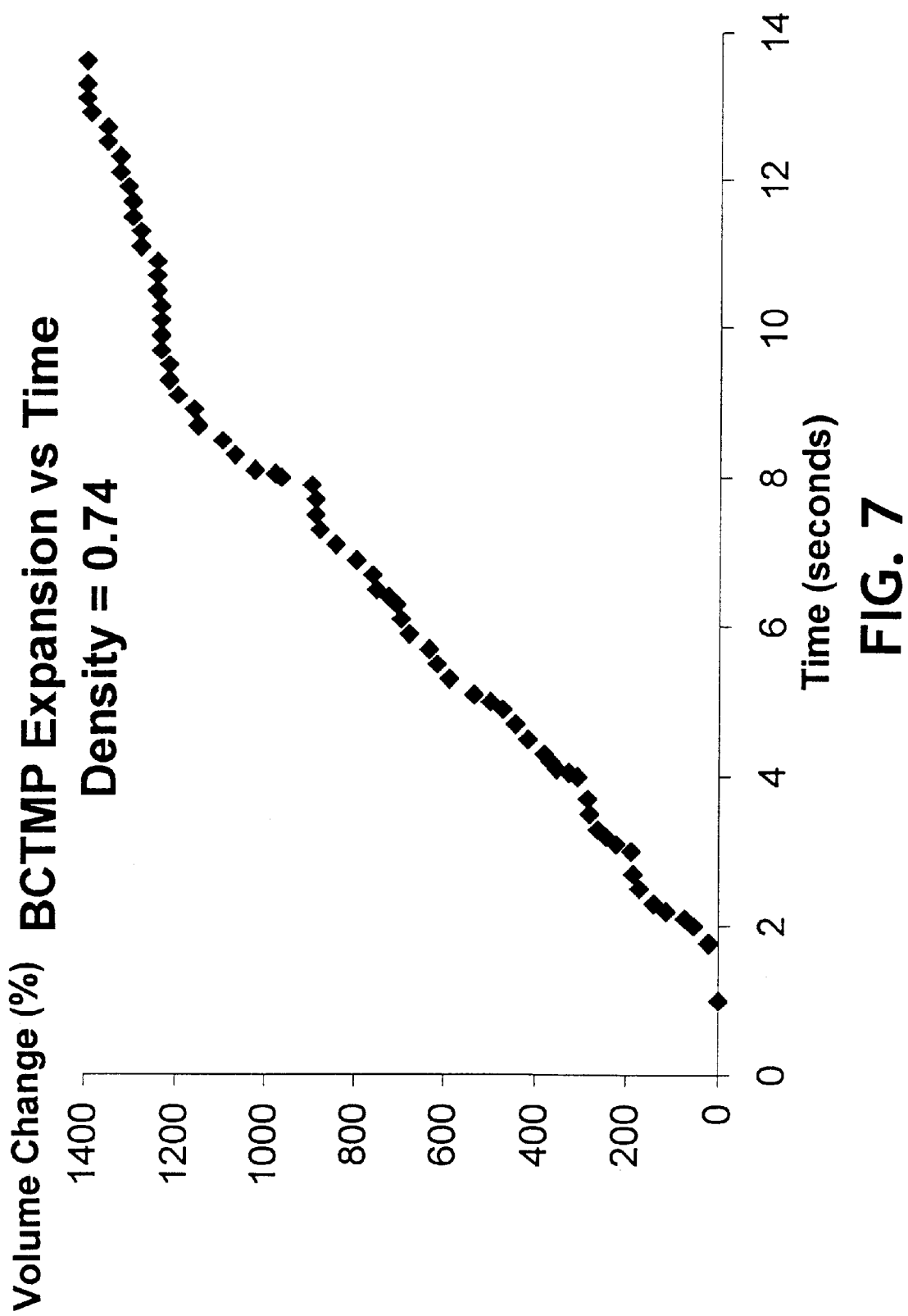
FIG. 7 is a graph of an absorbent member, formed from bleached chemi-thermo-mechanical pulp and having a density of 0.74 g/cc, which compares volume change measured as a percentage along the y-axis, to a change in time measured in seconds along the x-axis.
Figure 8:
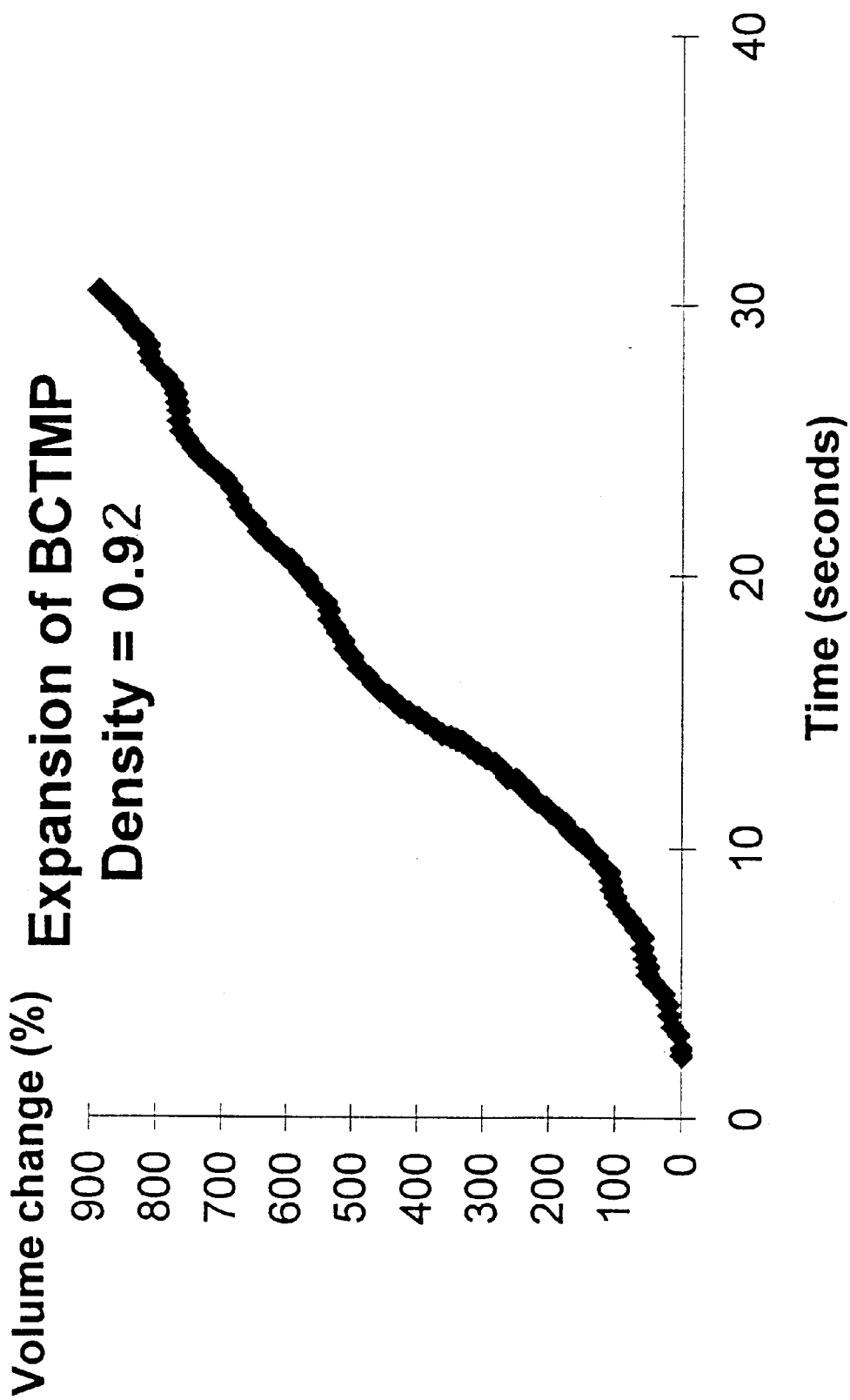
FIG. 8 is a graph of an absorbent member, formed from bleached chemi-thermo-mechanical pulp and having a density of 0.92 g/cc, which compares volume change measured as a percentage along the y-axis, to a change in time measured in seconds along the x-axis.

FIGS. 6–8 represent three curves generated using the above test procedure. The absorbent member 10 in FIG. 6 had a density of 0.66 g/cc, the absorbent member 10 in FIG. 7 had a density of 0.74 g/cc, and the absorbent member 10 in FIG. 8 had a density of 0.92 g/cc. The three graphs clearly show that the volume change of the sample increased over time.

EXAMPLE 1

A small cube (approximately 2.54 cm×2.54 cm ×1.4 cm) of the absorbent member 10 was placed into a large pan of water which had a one inch grid marked on the bottom of the pan. High speed video photography (500 frames per second) was used to take pictures of the cube as it expanded upon being dropped into the pan of water. For a cube with the density of approximately 0.74 gram/cc, the initial or first second was very slow expansion, about 29% volume change per second. The next eight seconds, from 1 to 8 seconds, revealed a very rapid expansion rate of about 156% volume change per second (about 14.09 cc/second). The expansion rate then dropped off to about 47% volume change per second for the remainder of the test and expansion stopped completely at about 12 seconds. This expansion performance of a sample is related to the "surface area to volume ratio" which is calculated to be r=3 cm$^{-1}$ for this cube. The higher this number, the quicker the total expansion occurs and the higher the expansion rate.

However, it should be noted that for equal density and shape, the absorbent member 10 will absorb faster and hence expand much faster than other absorbent members constructed from cellulosic fibers. The "amount of expansion" is defined for purposes of this invention as the distance the absorbent member 10 will expand in a given direction once the absorbent member 10 is wetted by an aqueous fluid, such as water. The greater the stress level within the dense absorbent member 10, the greater the "amount of expansion." Furthermore, the expansion of the absorbent member 10 begins once the absorbent member 10 is wetted by an aqueous fluid.

Experimental testing has shown that the cellulosic fibers 12 have a locked in potential energy that is released as a "dynamic" force when the absorbent member 10 is triggered by aqueous fluid. The amount of expansion can be 100% or greater, preferably the amount of expansion can be 500% or greater, more preferably, the amount of expansion can be 800% or greater, and most preferably, the amount of expansion can be 1,000% or greater. An amount of expansion of 800% in a particular direction, i.e. the x-direction of the absorbent member 10, is equivalent to an expansion of 8 times the original x dimension. This amount of expansion is fantastic and unheard of with most cellulosic fibers. The dynamic force or pressure (y) is empirically related to the expansion through the exponential relationship that approximates the curvature of the plotted data points. This plotted curve is best approximated by the formula y=ae$^{bx}$, where "a" is the maximum pressure exerted by the triggered absorbent member 10 upon its contact with an aqueous fluid; "e" is an exponential constant which is the irrational and transcendental number 2.71828, the base of Napier logarithms; the factor "b" is a constant value ranging between –0.015 and –0.045 which is a function of the maximum pressure and maximum volume change of the absorbent member 10, and "x" is the percent expansion or volume change of the absorbent member 10.

The potential energy (E) that can be recovered from the absorbent member 10 is E=–a/b. These are unique characteristics of a cellulosic absorbent member 10.

The following example illustrates this point.

EXAMPLE 2

Randomly oriented bleached chemi-thermo-mechanical cellulosic softwood fibers 12 were collected in a hopper, with a small amount of moisture, to a depth of approximately two inches (approximately 51 mm). The absorbent fibers were then compressed to 1/32 of an inch (about 0.8 mm) in the vertical or z-direction and dried to form an absorbent member 10. The stressed and compressed condition of the absorbent fibers 12 were held together by a plurality of hydrogen bonds 14, both intra fiber and inter fiber. Later, when the absorbent member 10 was wetted by an aqueous fluid, the hydrogen bonds were broken and the fibers returned to a relaxed unstressed condition which was an expansion causing the absorbent member 10 to increase in the z-direction to a dimension of about 1/4 of an inch (about 6.4 mm). This represented an "amount of expansion" of about 700% in the z-direction.

Figure 9:
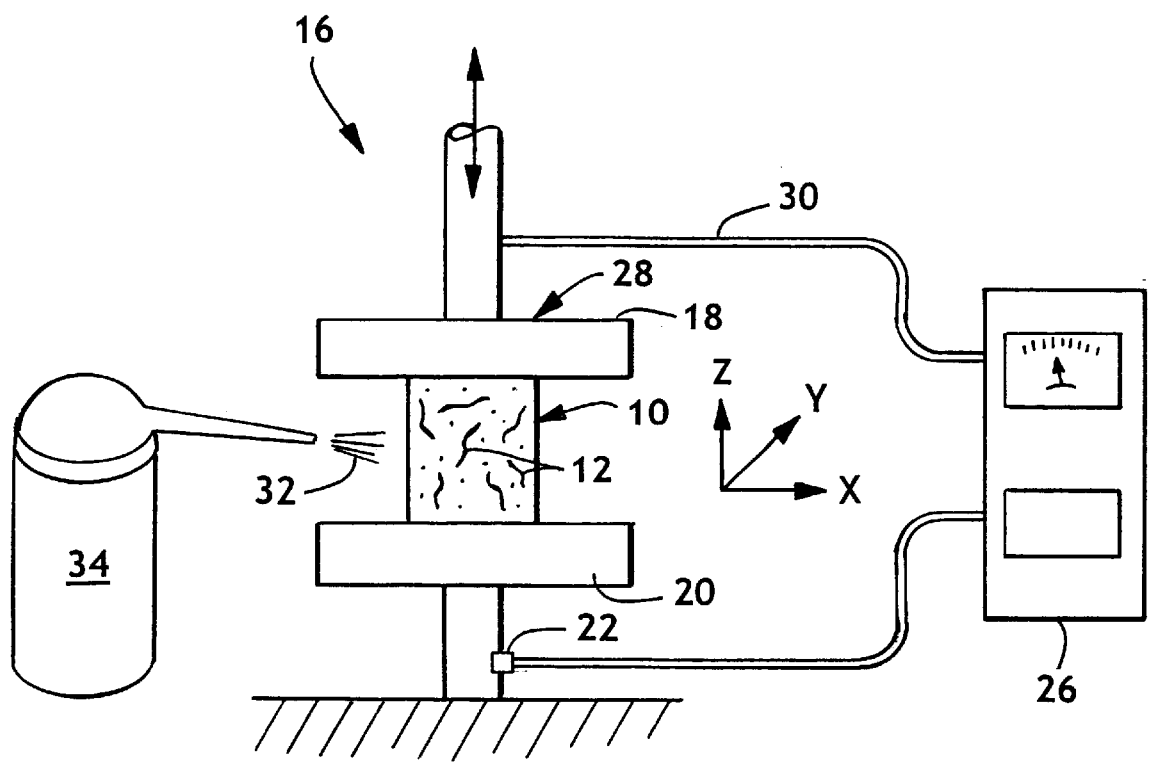
FIG. 9 is a schematic representation of an absorbent member positioned between two opposing platens which are mechanically and electrically connected to an Instron tester to record the pressure generated as the absorbent member expands.

Referring now to FIG. 9, a test apparatus 16 is depicted which includes an absorbent member 10 positioned between two opposing platens, 18 and 20 respectively. The platen 18 is capable of moving vertically up and down while the platen 20 is stationary. The platen 20 contains a load cell 22 which is electrically connected via lead 24 to an Instron Mini-55 tester 26. The Instron tester is commercially available from Instron Corporation having an office at 644 Busse Hwy. Park Ridge, Ill. 60068. The load cell 22 is capable of measuring the forces or pressures 28 applied against the upper and lower platens, 18 and 20 respectively, and which are being transmitted through the sample of the absorbent member 10.

The upper platen 18 is also electrically connected via a lead 30 to the Instron tester 26. The Instron tester 26 is capable of indicating and recording the pressure applied against the absorbent member 10 as well as the movement of upper platen 18 as the absorbent member 10 expands vertically, in the z-direction.

When an aqueous fluid 32, such as water, is sprayed from a spray bottle 34 onto the absorbent member 10, the cellulosic fibers 12 which form the network of fibers from which the absorbent member 10 is constructed will expand. If the absorbent member 10 is oriented in the test machine such that the force vector direction that imparted the stressed condition is perpendicular to the two platens, 18 and 20 respectively, it will expand vertically pressing against the platens 18 and 20. As the fibers 12 expand, an increase in pressure will be created against the two platens, 18 and 20 respectively. By measuring and recording the amount of force which is applied against the two platens, 18 and 20 respectively, at the respective expansion percentage, one can determine the "stored energy curve". This "stored energy curve" can be measured in energy per unit volume for the absorbent member 10 and can be used to predict the amount of work the absorbent member 10 can deliver toward absorbing fluid when incorporated into an absorbent product, for example, an infant diaper.

The following example illustrates this point.

EXAMPLE 3

An approximately cubic shaped piece of an absorbent member 10 was placed between the two platens, 18 and 20 respectively, and the upper platen 18 was moved vertically downward toward the lower platen 20 until a very slight pressure of approximately 0.5 pound per square inch (psi) was applied to the absorbent member 10. Water 32, contained in the spray bottled 34, was then sprayed onto the absorbent member 10 and this caused some of the hydrogen bonds to break. The hydrogen bonds were holding the fibers 12 together and restraining the fibers 12 in a stressed condition. As the hydrogen bonds broke, a rapid increase in force was indicated by the Instron tester 26. Since the absorbent member 10 did not have any measurable change in size in the cross section the pressure could be calculated. The higher the initial density of the absorbent member 10, the higher was the pressure that was generated. Additional water 32 was sprayed onto the absorbent member 10 until no additional increase in pressure was indicated by the Instron. The pressure value, at this zero or no change in volume point, was recorded so that it could be plotted out in graph form.

The next data point was then obtained by performing the following procedure. The upper platen 18 was raised approximately 0.5 mm and it was noticed that the pressure indicated by the Instron tester 26 dropped dramatically. Additional water 32 from the spray bottle 34 was then sprayed onto the absorbent structure 10. This additional water 32 caused more of the hydrogen bonds to break and allowed for additional vertical expansion of the absorbent member 10. The pressure was continuously indicated and additional water 32 was sprayed onto the absorbent member 10 until no additional increase in pressure could be recorded. This second maximum pressure was less than the maximum pressure indicated for the first data point but greater than the immediate pressure reading when the platen 18 was first raised 0.5 mm. The second data point was then recorded at the percentage volume change (0.5 mm divided by the original thickness, in millimeters, and multiplied by 100).

Again, the upper platen 18 was raised approximately another 0.5 mm and it was again noticed that the recorded pressure dropped dramatically. This procedure was repeated a number of times in order to obtain a plurality of data points which could be plotted on a chart in graph form. The maximum pressure at a given amount of expansion was recorded by the Instron tester 26. This procedure was repeated with gradually increasing separations of the two platens, 18 and 20 respectively, until the pressure value was not measurable on the Instron tester 26.

It should be noted that the distance the two platens, 18 and 20 respectively, are separated for each step of the above procedure is not critical. However, when the slope of the graph is changing dramatically, it is advantageous to plot the values at increments of about 0.5 mm and to use a larger separation, say 5 mm, when the slope tapers off along the horizontal axis.

After the absorbent member 10 had expanded to a point where the pressure value was not measurable on the Instron tester 26, the absorbent member 10 was then laid on its side (essentially zero pressure) and additional water 32 was added until the absorbent member 10 reached its maximum size. This maximum size usually represented a total increase of from between about 400% to about 800% in one direction (z). There was a minor amount of volume increase in the cross section but it was less than 20% increase in dimension in the x and y directions. A curve was then plotted on graph paper with each curve representing one sample of an absorbent member 10 at a particular density value.

Figure 10:
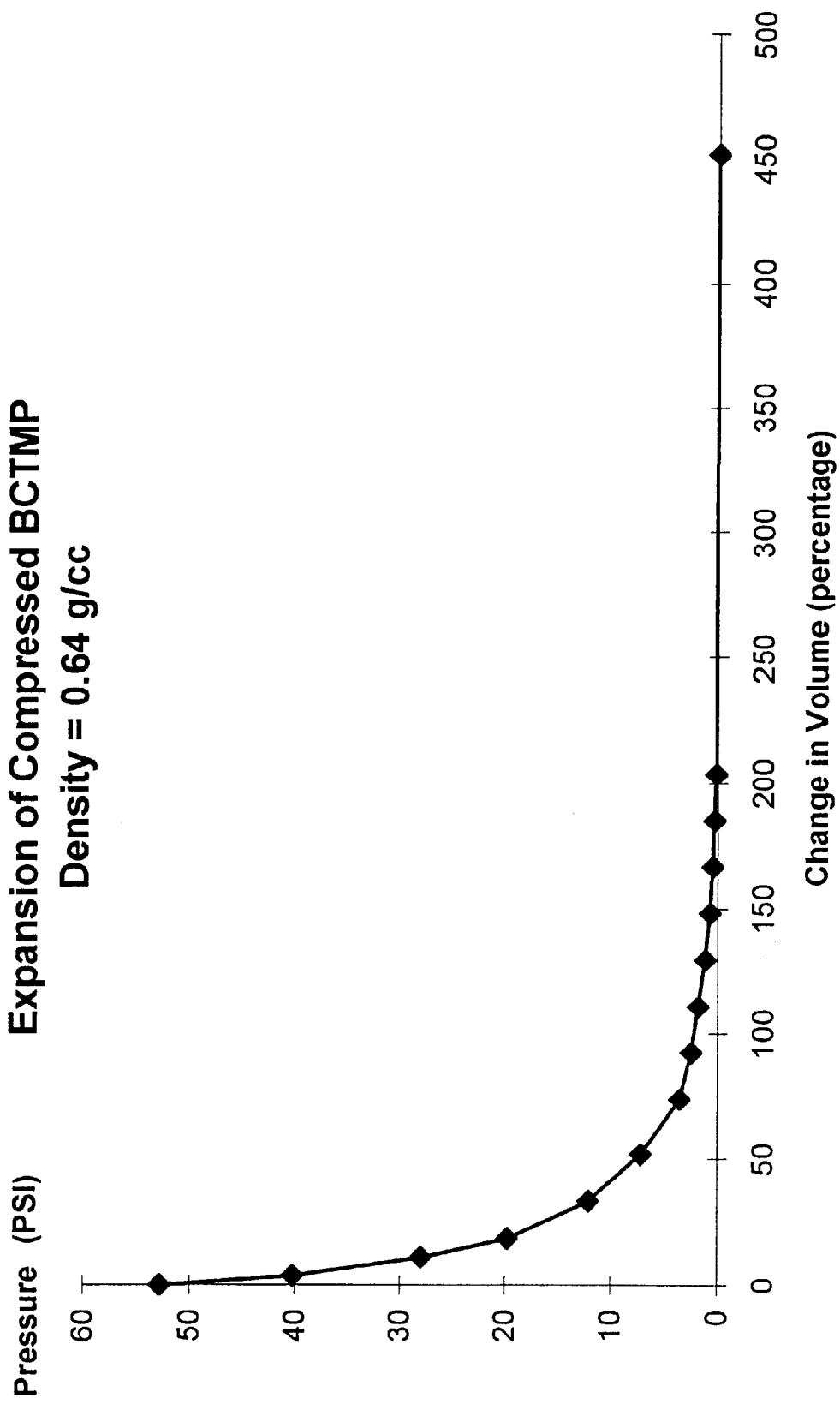
FIG. 10 is a graph of an absorbent member, formed from bleached chemi-thermo-mechanical pulp and having a density of 0.64 g/cc, which compares the pressure needed to constrain expansion of the absorbent member, measured in psi along the y axis, to a change in volume, measured along the x-axis.
Figure 11:
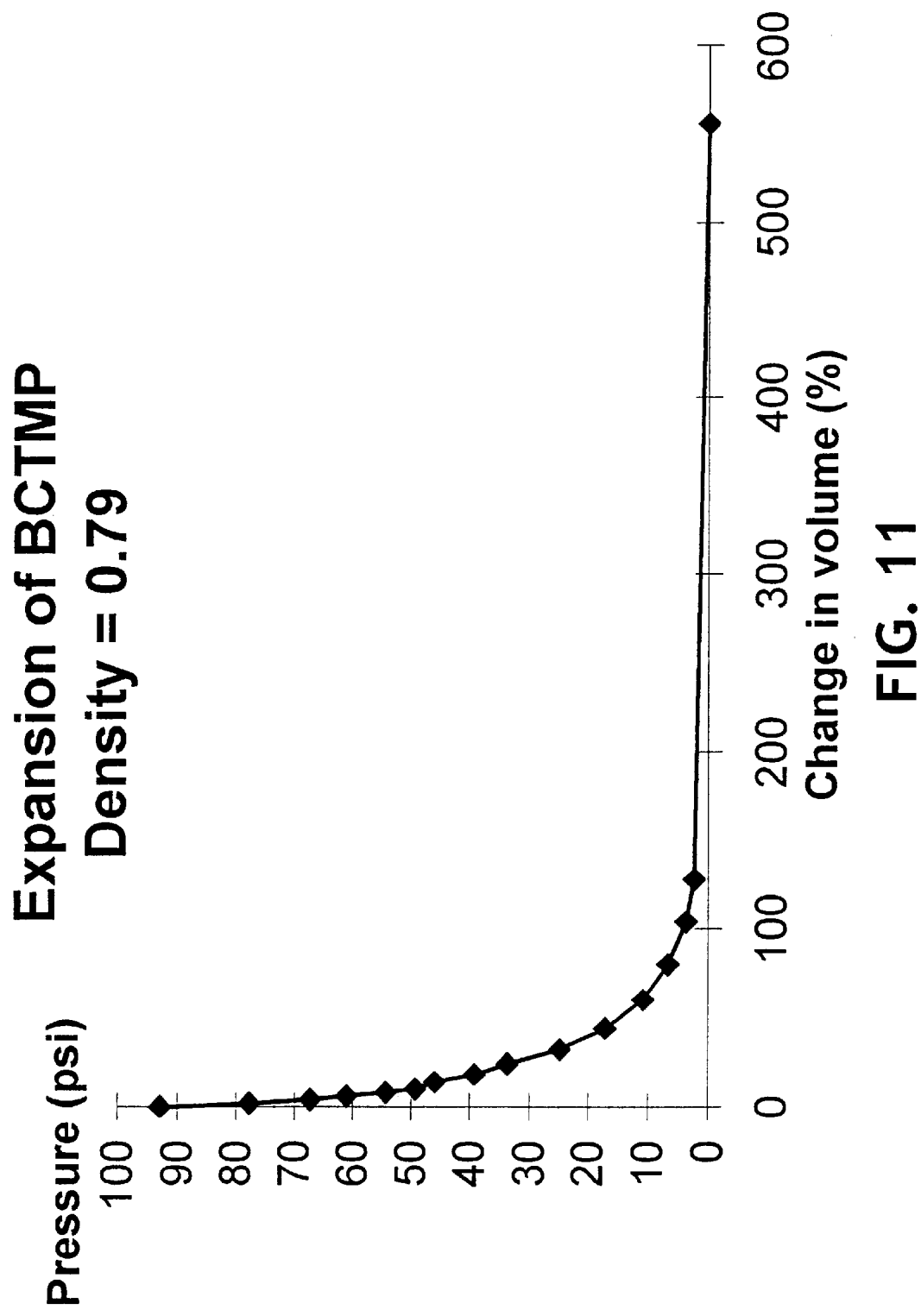
FIG. 11 is a graph of an absorbent member, formed from bleached chemi-thermo-mechanical pulp and having a density of 0.79 g/cc, which compares the pressure needed to constrain expansion of the absorbent member, measured in psi along the y axis, to a change in volume, measured along the x-axis.
Figure 12:
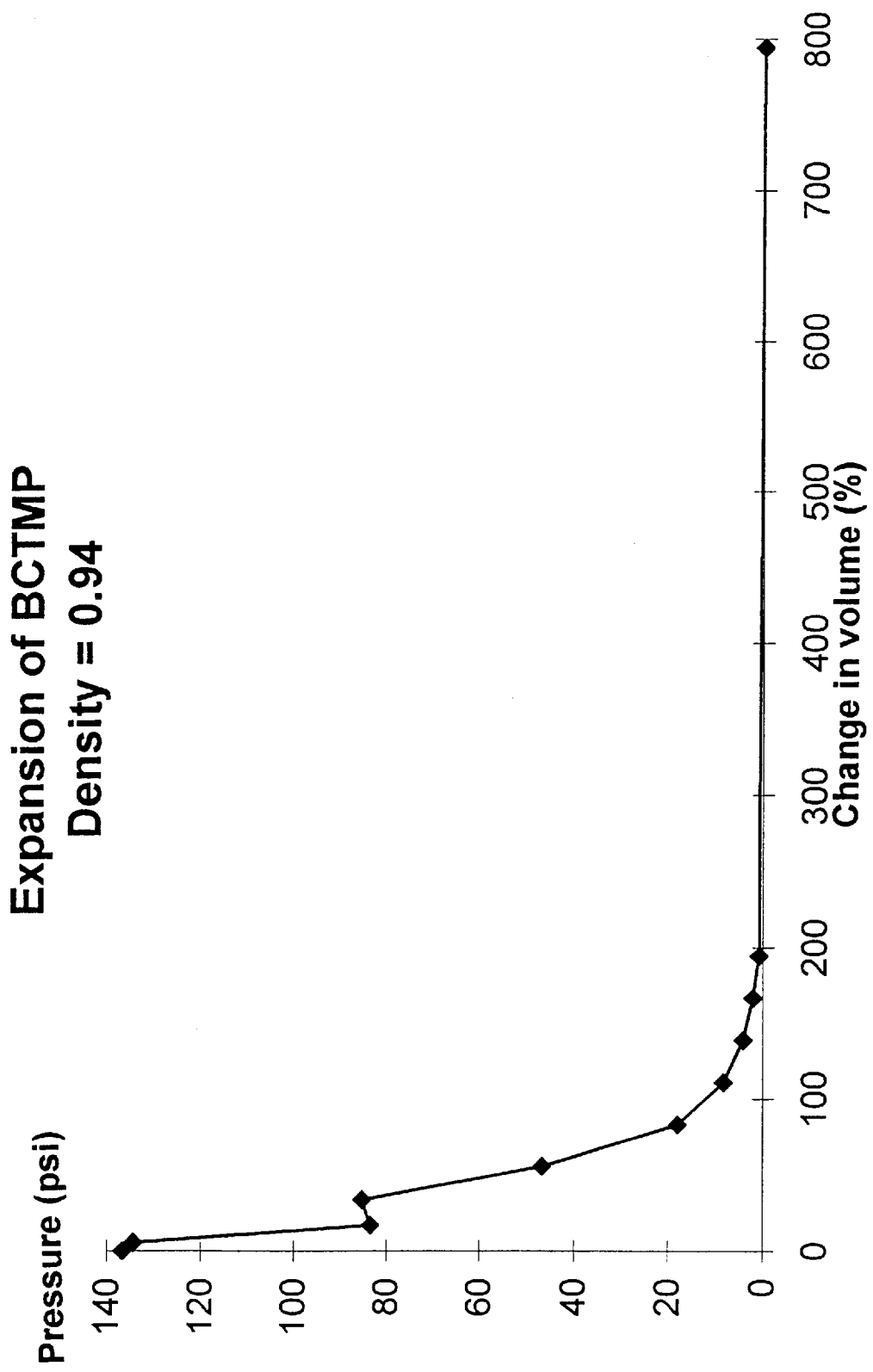
FIG. 12 is a graph of an absorbent member, formed from bleached chemi-thermo-mechanical pulp and having a density of 0.94 g/cc, which compares the pressure needed to constrain expansion of the absorbent member, measured in psi along the y axis, to a change in volume, measured along the x-axis.

FIGS. 10–12 represent three curves generated using the above test procedure. The absorbent member 10 in FIG. 10 had a density of 0.64 g/cc, the absorbent member 10 in FIG. 11 had a density of 0.79 g/cc, and the absorbent member 10 in FIG. 12 had a density of 0.94 g/cc. The three graphs clearly show that as the density of a sample increased, the maximum pressure needed to constrain its expansion increased. Stated another way, the stored and recoverable energy increased as the density of a sample increased.

The absorbent member 10 constructed as taught above functions in a unique way compared to most traditional low density cellulosic absorbent members. The driving force of liquid absorption is the capillaries where the liquid surface tension acts on the capillary boundaries so that the pressure is highest with smaller capillaries. Of two absorbent members 10, the one with the higher bulk density will have the smaller capillaries but higher driving pressure. There is a force opposing flow due to viscous shear within the liquid that is touching the capillary boundary walls which is proportional to the advancing liquid velocity and acts upon the perimeter of the capillaries. As the capillaries decrease in size, the flow will slow down due to this force. The absorbent member 10 of this invention, however, has an unexpected behavior that allows the capillaries to grow in effective diameter as soon as it is contacted by an aqueous fluid. When the hydrogen bonds of the stressed and compacted absorbent member 10 are broken, the volume expansion creates larger and new capillaries while the leading liquid front and the driving force is still accelerating the fluid behind it. This is the opposite result from what one will see when an absorbent member is made from a traditional chemical pulp, for example, Kraft pulp, that is contacted by an aqueous fluid. In a traditional pulp fiber, the capillaries tend to collapse when the fibers are wetted.

The absorbent member 10 will operate in a manner opposite to most traditional low density southern softwood Kraft absorbent members. The first insult of aqueous fluid into a low density traditional absorbent member begins to collapse the fiber structure due to the surface tension of the fluid and the limpness of the fibers. Conversely, the absorbent member 10 of this invention rapidly expands with the first insult of fluid which causes some of the hydrogen bonds to break and allows the stressed and contorted stiff fibers 12 to return to an unbent or more relaxed condition, i.e. to the approximate condition they were in before being stressed or compressed. This structural response is virtually an accelerating force moving fluid into the absorbent member 10 versus the decelerating force which is more typical with a low density Kraft absorbent member. Because the absorbent member 10 is of a high density and the Kraft absorbent member is of a low density, the forces and absorbent rates will be different, yet the changes in force and rates will occur as indicated.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An absorbent member exhibiting exceptional expansion properties when wetted, said absorbent member consisting of a multitude of randomly oriented chemi-thermo-mechanical cellulosic fibers having an average length from about 1 mm to 5 mm and containing at least about 20% lignin within said cellulosic fibers, said absorbent member having a moisture content of from between about 1% to about 20% water by weight of fiber, said fibers being compacted and bonded by hydrogen bonds and being retained in a stressed condition, said hydrogen bonds being breakable upon contact with an aqueous fluid thereby allowing rapid expansion of said absorbent member, and said absorbent member having a density of from between about 0.5 g/cc to about 1 g/cc.

2. The absorbent member of claim 1 wherein said cellulosic fibers have been stressed from a non-stressed condition wherein said cellulosic fibers had a bulk density of from between about 0.01 g/cc to about 0.1 g/cc.

3. The absorbent member of claim 2 wherein said cellulosic fibers in a stressed condition have a density of from between about 0.5 g/cc to about 0.8 g/cc.

4. An absorbent member having a high absorbent capacity and exhibiting exceptional expansion properties when wetted by an aqueous fluid, said absorbent member consisting of a multitude of randomly oriented chemi-thermo-mechanical cellulosic fibers having an average length of from between about 1 mm to 5 mm, said fibers formed from softwood and containing at least about 20% lignin within said fibers, said absorbent member having a moisture content of from between about 1% to about 20% water by weight of fiber and having a density of from between about 0.5 g/cc to about 1 g/cc, and said fibers being compacted and bonded by hydrogen bonds and retained in an elastically stressed condition, said hydrogen bonds being breakable upon contact with an aqueous fluid thereby allowing rapid expansion of said absorbent member.

5. The absorbent member of claim 4 wherein said moisture content ranges from between about 5% to about 15% water by weight of fiber.

6. The absorbent member of claim 4 wherein said cellulosic fibers have an average length of from between about 1 to about 3 millimeters.

7. The absorbent member of claim 4 wherein said cellulosic fibers have an average diameter of from between about 10 to about 40 microns.

8. The absorbent member of claim 4 wherein said cellulosic fibers have been stressed from a non-stressed condition wherein said cellulosic fibers had a bulk density of from between about 0.01 g/cc to about 0.1 g/cc.

9. An absorbent member having a high absorbent capacity and exhibiting exceptional expansion properties when wetted by an aqueous fluid, said absorbent member consisting of a multitude of randomly oriented stiff chemi-thermo-mechanical cellulosic fibers having an average length of from between about 1 mm to about 5 mm, said fibers formed from softwood and containing at least about 20% lignin within said fibers, said absorbent member having a moisture content of from between about 2% to about 15% water by weight of fiber and having a density of from between about 0.5 g/cc to about 0.8 g/cc, and said fibers being compacted and bonded by hydrogen bonds and retained in an elastically stressed condition, said hydrogen bonds being breakable upon contact with an aqueous fluid thereby allowing rapid expansion of said absorbent member.

10. The absorbent member of claim 9 wherein said chemi-thermo-mechanical fibers are bleached.

11. The absorbent member of claim 9 wherein at least a portion of said cellulosic fibers have a non-linear configuration.

12. The absorbent member of claim 9 wherein said fibers, when retained in an elastically stressed condition, exhibit recoverable bending, compression and shear forces.

13. An absorbent member having a high absorbent capacity and exhibiting exceptional expansion properties when wetted by an aqueous fluid, said absorbent member consisting of a multitude of randomly oriented chemi-thermo-mechanical cellulosic fibers having an average length of from between about 1 mm to about 5 mm and containing at least about 20% lignin within said cellulosic fibers, said absorbent member having a moisture content of from between about 5% to about 15% water by weight of fiber and having a density of from between about 0.5 g/cc to about 0.8 g/cc, and said fibers being compacted and bonded by hydrogen bonds and retained in an elastically stressed condition, said hydrogen bonds being breakable upon contact with an aqueous fluid thereby allowing rapid expansion of said absorbent member.

14. The absorbent member of claim 13 wherein said cellulosic fibers have been stressed from a non-stressed condition wherein said cellulosic fibers had a bulk density of from between about 0.01 g/cc to about 0.1 g/cc.

15. The absorbent member of claim 13 wherein said absorbent member contains a potential energy that can be recovered according to the formula $E=-a/b$ where: "E" is the potential energy that can be recovered from the absorbent member: "a" is the maximum pressure exerted by the triggered absorbent member upon its contact with an aqueous fluid: and "b" is a constant value ranging between $-0.015$ and $-0.045$ which is a function of the maximum pressure and maximum volume change of the absorbent member.

16. The absorbent member of claim 13 wherein said cellulosic fibers have an average length of from between about 1 to about 3 millimeters.

17. The absorbent member of claim 13 wherein said chemi-thermo-mechanical fibers are softwood fibers.

18. The absorbent member of claim 17 wherein said softwood fibers are bleached.

* * * * *